United States Patent [19]

Li et al.

[11] Patent Number: 5,221,724
[45] Date of Patent: Jun. 22, 1993

[54] POLYSILOXANE POLYUREA URETHANES

[75] Inventors: Chi Li; Stuart L. Cooper, both of Madison, Wis.

[73] Assignee: Wisconsin Alumni Research Foundation, Madison, Wis.

[21] Appl. No.: 617,401

[22] Filed: Nov. 19, 1990

Related U.S. Application Data

[63] Continuation of Ser. No. 318,491, Mar. 2, 1989, abandoned, which is a continuation of Ser. No. 87,783, Aug. 12, 1987, abandoned.

[51] Int. Cl.$^5$ .............. C08G 77/458; 528 28; 528 29; 528 38; 525 452; 525 453; 525 454
[52] U.S. Cl. .................. 528/28; 528/29; 528/38; 525/453
[58] Field of Search .............. 528/28, 29, 38; 525/452, 453, 454

[56] References Cited

U.S. PATENT DOCUMENTS

| | | | |
|---|---|---|---|
| 2,907,782 | 10/1959 | Pike | 528/28 |
| 3,666,726 | 5/1972 | Grogler et al. | 528/28 |
| 4,002,794 | 1/1977 | Schwarcz | 428/352 |
| 4,164,491 | 8/1979 | Itoh et al. | 260/37 SB |
| 4,312,920 | 1/1982 | Pierce et al. | 428/425.5 |
| 4,504,313 | 3/1985 | Robertson | 528/28 |
| 4,528,343 | 7/1985 | Kira | 528/26 |
| 4,605,712 | 8/1986 | Mueller et al. | 528/29 |
| 4,631,329 | 12/1986 | Gornowicz | 528/28 |
| 4,644,046 | 2/1987 | Yamada | 528/28 |

FOREIGN PATENT DOCUMENTS 0182254 10/1984 Japan .
2073219 10/1981 United Kingdom .

OTHER PUBLICATIONS

"Properties of Polyether-Polyurethane Zwitterionomers" Hwang et al., *Polymer Engineering and Science,* Oct. 1981, vol. 21, No. 15 pp. 1027-1036.

"Segmented Organosiloxane Copolymers: I. Synthesis of Siloxane-Urea Copolymers" Yilgor et al., *Polymer,* Dec. 1984 vol. 25 pp. 1800-1806.

"Segmented Organsiloxane Copolymers: II Thermal and Mechanical Properties of Siloxane-Urea Copolymer" Yilgor et al., *Polymer,* Dec. 1984 vol. 25, pp. 1807-1816.

Chen-Tsai et al., *Polymer,* 27, 659-666 (1986).

Speckhard et al., *Rubber Chemistry and Tech.,* 59, 405-431 (1986).

Yu et al., "Polydimethylsiloxane-Polyurethane Elastomers: Synthesis and Properties of Segmented Copolymers and Related Zwitterionomers," *J. Polym. Sci., Polymer Phys. Ed.,* 23, 2319-2338 (1985).

Yu et al., "Properties of Ultraviolet Cured Polydimethyl Siloxane-Urea Acrylates," *J. App. Polym. Sci.,* 30, 2115-2135 (1985).

*Primary Examiner*—Ralph H. Dean, Jr.
*Attorney, Agent, or Firm*—Olson & Hierl, Ltd.

[57] ABSTRACT

Polysiloxane-containing polyurea and polyurea urethane block copolymers and devices formed therefrom are biocompatible and demonstrate improved physical and mechanical properties. The pre-reaction of an amine-terminated polysiloxane soft segment with an organic diisocyanate provides an oligomer that enhances the hydrophilic properties of the copolymer.

34 Claims, 12 Drawing Sheets

POLYSILOXANE POLYUREA URETHANES

This invention was made with U.S. government support awarded by the Department of the Navy (DOD), Grant Number N00014-83-K-0423. The U.S. Government has certain rights in this invention.

CROSS REFERENCE TO RELATED APPLICATION

This application is a continuation of application Ser. No. 318,491, filed Mar. 2, 1989, now abandoned, which is a continuation of application Ser. No. 087,783, filed Aug. 12, 1987, now abandoned.

TECHNICAL FIELD

The present invention relates to segmented polyurea urethane and polyurea block copolymers which include modified-polysiloxane soft segments and which provide hydrophilic materials having improved physical properties including tensile strength, flexibility and abrasion resistance.

BACKGROUND OF THE INVENTION

The properties of a polymer are of great importance in any application. For biomedical polymers, the most important single property is probably biocompatibility, which refers to the interactions of living body tissues, compounds and fluids including blood with any implanted or contacting polymeric material. Each system of polymer-body tissue interactions must be studied individually in terms of physical properties including tensile strength, modulus (flexibility) and abrasion resistance, polymer stability, general tissue-fluid interactions and blood compatibility.

Polyurethane block copolymers have been proposed for use in blood-contacting applications because of their generally excellent physical properties and relatively good blood compatibility. Lelah and Cooper, *Polyurethanes in Medicine*, CRC Press, Boca Raton, Fla. (1986). Thermoplastic polyurethane block copolymers of the $(AB)_n$ type have alternating soft and hard segments. In conventional segmented linear polyurethanes, the soft segments are often low molecular weight (600–3000) polyether or polyester macroglycols, and the hard segments usually comprise an aromatic diisocyanate that has been chain extended with a short chain diol.

It is desirable to further improve the blood compatibility of these materials to allow their use in such demanding applications as small-diameter vascular grafts, catheters, kidney dialyzers, cardiac assist devices and the artificial heart.

A segmented polyurethane can exhibit a wide range of physical properties and morphologies depending on the chemical structure of the soft and hard segments. The soft segments provide flexibility, whereas the hard segments are more rigid and provide tensile strength and wear or abrasion resistance. In general, segmented polyurethanes demonstrate excellent mechanical properties which are directly related to their two phase morphology.

Polysiloxane-based elastomers, and in particular polydimethylsiloxane-based materials, demonstrate desirable characteristics including extremely low glass transition temperatures ($T_g$), good thermal and oxidative stabilities, low surface energies and good electric properties. Because of their good biocompatibility and low toxicity, polydimethylsiloxanes have been used in biomedical applications. A. Braley, *J. Macromol. Sci., Chem.*, A4, 529 (1970) and Ward, Jr. et al., *Organometallic Polymers*, Academic Press, New York (1978).

Low molecular weight polydimethylsiloxanes (PDMS) have been incorporated as soft segments in polyurethane block copolymers. Yu et al., *J. Polym. Sci., Polym. Phys. Ed.*, 23, 2319 (1985) and G. L. Gains, *Macromolecules*, 14 208 (1981). As a result of the large difference in the solubility parameters of soft and hard segments, however, these polydimethylsiloxane-based polyurethanes are likely to be highly phase-separated materials resulting in rather poor mechanical properties. Yu et al., id. and Speckhard et al., *Rubber Chem. and Tech.*, 59, 405 (1986). Premature phase separation may also occur during synthesis of these materials to produce compositional heterogeneity and low overall molecular weight. Speckhard et al., id.

In accordance with several studies concerning the physical properties of polydimethylsiloxane-based polyurethane block copolymers (Speckhard et al., id. and Yu et al., id.), increases in the degree of phase mixing and improvement in the hard domain cohesion can lead to enhanced physical properties. For example, improved tensile properties for poly(chloropropylmethylsiloxane) polyurethanes and poly(cyanoethylmethylsiloxane) polyurethanes have been obtained following the introduction of polar side groups along the polydimethylsiloxane soft segment backbone [Yu et al., id. and Li et al., id.]. These polar side groups promote phase mixing and improve interfacial adhesion which are important factors in determining the mechanical properties of the two-phase materials.

A continuing need exists for improved polymeric materials that are suitable for blood-contacting applications and which exhibit the necessary tensile properties and abrasion resistance for long-term use.

SUMMARY OF THE INVENTION

The present invention relates to hydrophilic segmented polyurea urethane and polyurea block copolymers that include an organic diisocyanate-modified amine-terminated polysiloxane soft segment.

The soft segment comprises an oligomer that includes the reaction product of an organic diisocyanate and an amine-terminated polysiloxane represented by the formula:

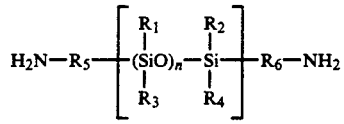

wherein n is an integer from 1 to about 200; $R_1$, $R_2$, $R_3$ and $R_4$ can be selected independently from any linear or branched hydrocarbon radical containing from 1 to about 8 carbon atoms; and $R_5$ and $R_6$ can be selected independently from any linear or branched hydrocarbon radical containing from 1 to about 16 carbon atoms. Thus, $R_1$–$R_6$ can be an aliphatic radical such as methyl, ethyl, propyl, butyl, isobutyl, pentyl, hexyl, vinyl, allyl, butenyl and hexenyl groups; a cycloaliphatic radical such as cyclohexyl and cyclohexenyl groups; or a phenyl radical. $R_1$–$R_6$ can also include substituted radicals such as halo-substituted and cyano-substituted groups. $R_5$ and $R_6$ can further include linear, branched and cyclic $C_9$–$C_{16}$ groups.

The hard segment of the copolymer can include an aromatic or aliphatic diisocyanate which has been chain-extended with a $C_2$–$C_{20}$ alkyl or aryl diol or diamine. In an additional embodiment, zwitterionomers are prepared by quaternizing the tertiary amine of the organic diisocyanate-extended material with 1,3-propane sulfone.

The organic diisocyanate used in the formation of the oligomer and as the organic diisocyanate of the hard segment can include 2,4-toluene diisocyanate, 2,6-toluene diisocyanate, isomeric mixtures of 2,4- and 2,6-toluene diisocyanate, methylene bis(p-phenyl isocyanate), 1,5-naphthalene diisocyanate, methylene bis(p-cyclohexyl isocyanate), 1,6-hexane diisocyanate, isophorone diisocyanate, and cyclohexyl diisocyanate or any other diisocyanate having a $C_4$–$C_{20}$ alkylene or arylene group. In addition, mixtures of two or more species or types of diisocyanate can be used.

The diol or diamine can comprise any short chain diol or diamine having a $C_2$–$C_{20}$ alkyl or aryl group including 1,4-butanediol, ethylene glycol, hexanediol, ethylene diamine, hexamethylene diamine, 4-aminobenzylamines, 4-4'-diamino-dicyclohexyl methane, phenylene diamines, toluene diamines, 4,4'-methylene bis(2-chloroaniline), 4,4-diaminodiphenyl sulfone and 4,4-diaminodiphenyl ether or mixtures of diols or diamines.

The present invention also relates to a method of producing the copolymers described herein and medical devices formed with the copolymers of this invention. Such devices are useful in applications where a biocompatible material is needed to avoid or minimize adverse reactions upon contact with blood or tissue.

The copolymer may comprise all of the device or only the surface which will be in contact with the body fluids. In particular, these materials may be used as vascular prostheses in the veinous or arterial system, as heart patches or as heart valves, as the outer encapsulant of implantable devices such as heart pacemakers, and as catheters or the outer sheath of catheters in contact with body fluids and the like. They may also be used as temporary coverings for skin loss resulting from either mechanical damage or burns, or they may be used as a covering for open wounds. Additionally these devices may be used as extra-corporeal devices to provide biocompatible channels through which body fluids may be passed in heart-lung and kidney machines, for example. Indeed the materials of these devices generally have the properties of semipermeable membranes and may be used as such in extracorporeal devices.

The effect of chemical structure on the extent of phase separation and the physical properties of the materials can be studied using a variety of techniques including thermal analysis, dynamic mechanical spectroscopy, tensile testing and small angle X-ray scattering.

One advantage of the present invention is the improved compatibility between the non-polar polysiloxane soft segments and the polar urethane hard segments when the polysiloxane soft segments are prereacted with an organic diisocyanate, and in particular an aliphatic diisocyanate.

Another advantage of the invention is the enhanced aggregation of hard segments by increasing the hard segment content or by the introduction of ionic functionality.

A further advantage is higher tensile strength, modulus and abrasion resistance of the present materials as compared to those polyurethanes which contain soft segments based on unmodified polysiloxane derivatives.

Numerous other advantages and benefits of the present invention will become more readily apparent based on the following description of a preferred embodiment of the invention.

DETAILED DESCRIPTION OF THE INVENTION

I. Introduction

Figure 1:
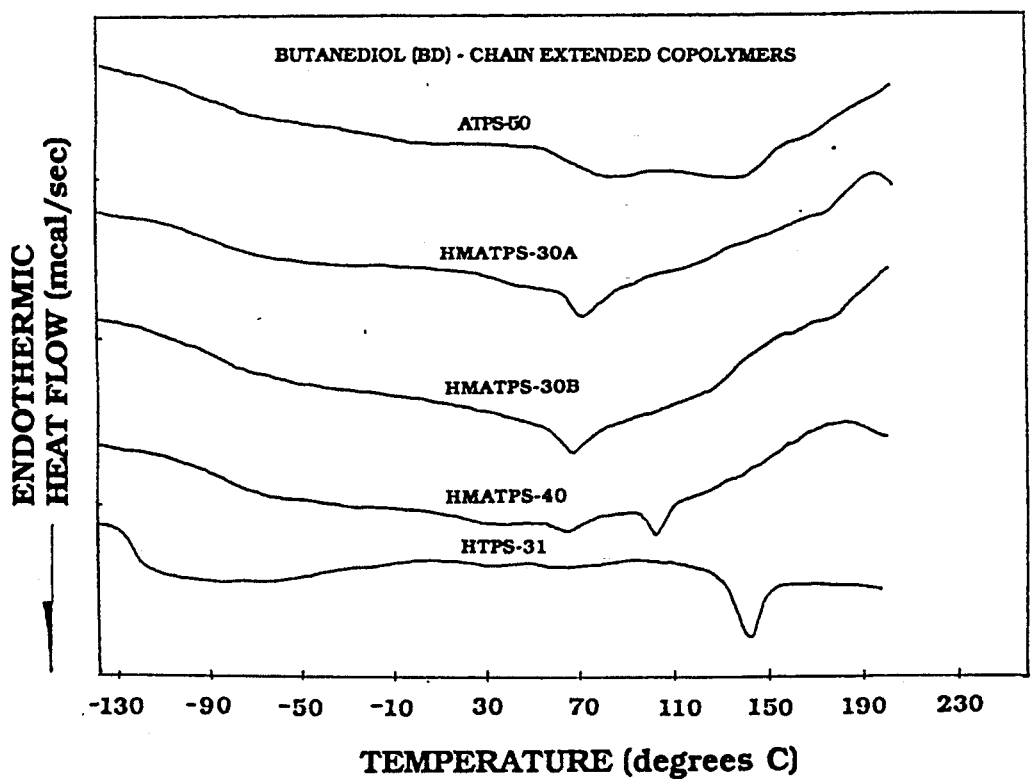
FIG. 1 illustrates differential scanning calorimetry (DSC) curves of the 1,4-butanediol (BD) chain extended materials.

For purposes of illustrating the present invention and the practice thereof, the method of preparing the present polyurethane block copolymers and the preparation of certain oligomers is described with reference to particular examples of copolymers and testing procedures for determining bulk and surface characteristics of those copolymers. It will be understood, however, that the copolymers of this invention are not limited only to those materials specifically described herein.

In accordance with the present invention, modifications to the polymer chain are performed, and bulk characterization techniques are used to analyze properties such as microphase separation. Bulk properties are related to surface properties, and the resulting polyurethanes can be evaluated for blood compatibility, for example, through a canine ex vivo blood-contacting experimental procedure. Although bulk modifications are performed, it should be recognized that the present polymer compositions can readily be used for coatings, or can be adapted for use as surface modifying agents.

A. Materials and Methods 1,3-bis(α, ω-aminopropyl)tetramethyldisiloxane (ATDS), (Silar Laboratories, Inc., Scotia, N.Y.) and 1,6-hexane diisocyanate (HDI) (Aldrich Chemical Co., Milwaukee, Wis.) were used without further purification. 4,4'-Diphenylmethane diisocyanate (MDI) (Polysciences Inc., Warrington, Pa.) was melted and purified by pressure filtration at 55 degrees Centigrade (C.). 1,4-Butanediol (BD), N-methyl diethanolamine (MDEA) and ethylene diamine (ED) were obtained from Aldrich Chemical Co. and were vacuum distilled before use. Octamethylcyclotetrasiloxane (D4) (Petrarch Systems, Inc., Bristol, Pa.) was distilled and dried over Fisher 4A molecular sieves. Stannous octoate (M&T Chemicals, Inc., Rathway, N.J.) and 1,3-propane sulfone (Aldrich Chemical Co.) were used as received.

B. Preparation of Oligomers and Copolymers

An α,ω-bis aminopropyl-polydimethylsiloxane oligomer (ATPS-6) was synthesized according to procedures described in Yu et al., *J. Polym. Sci., Polym. Phys. Ed.*, 23, 2319 (1985), which is incorporated herein by reference. The number average molecular weight of this oligomer was determined to be 600±1 by titration with 0.100 Normal HCl solution. Methyl red was used as the indicator. Proton NMR spectra confirmed the structure of this oligomer [Tyagi et al., *Polymer*, 25, 1807 (1984)].

Amine-terminated polydimethylsiloxane oligomers linked by HDI, HMATPS and segmented polyurea urethanes were synthesized in N,N-dimethylacetamide (DMA) solution by a series of condensation reactions. 0.02 Mole of ATPS-6 was dissolved in 40 milliliters (ml) of DMA in a three-neck flask fitted with a thermometer, condenser, nitrogen inlet, heating device and magnetic stirrer. 0.01 Mole of HDI and 3 drops of stannous octoate were added to the flask. The temperature was raised to 55°–60 degrees C. and maintained at that temperature for 1.5 hours. At that point, a FTIR spectra confirmed the absence of free isocyanate (NCO) groups. This intermediate product, which is the HDI-modified polydimethylsiloxane oligomer, was used in the synthesis of segmented polyurea urethanes. The number average molecular weight of this oligomer was 1410±10 as determined by HCl titration.

A second HMATPS oligomer was synthesized in the same manner but at a 2:3 molar ratio of HDI to ATPS-6. This stoichiometry produced an oligomer having a number average molecular weight 2070±10. The oligomers of the invention preferably have a molar ratio of organic diisocyanate to polysiloxane from about 1:2 to about 4:5 of which the foregoing two oligomers are representative.

0.02 Mole of MDI was dissolved in 20 ml of DMA in another three-neck flask fitted in the manner described above. The solution was heated to 60 degrees C. at which time the DMA solution of the HDI-modified polydimethylsiloxane oligomer was slowly added. The reaction temperature was maintained between 60-65 degrees C. for one hour. 0.01 Mole of 1,4-butanediol dissolved in 2 ml DMA with 3 additional drops of catalyst was then added into the flask. The chain extension reaction was carried out at 60–70 degrees C. for three hours. In the cases where ED and MDEA chain extenders were used, the catalyst was not used and the reaction solution was cooled to 30 degrees C. before addition of these reactants to avoid possible crosslinking caused by the highly exothermic chain extension reaction. The segmented polyurethanes were precipitated and washed in methanol, then filtered and dried in a vacuum oven at 45 degrees C. for about one week.

Thus, a polysiloxane-containing block copolymer of this invention is based on (a) an oligomer comprising the reaction product of (i) a first organic diisocyanate and (ii) a polysiloxane as described above; (b) a second organic diisocyanate; and (c) a $C_2$–$C_{20}$ alkylene or arylene diol or diamine. The mole ratio of oligomer to second organic diisocyanate to diol or diamine is preferably from about 2:1:1 to about 20:19:1, and more preferably from about 2:1:1 to about 8:7:1.

The chemical compositions of the representative oligomers and copolymers described herein are listed in Table I. A polymer made from 1 mol 600-MW amine-terminated polydimethylsiloxane (ATPS-6), 2 mol HDI and 1 mol BD is designated HMATPS-9. The code indicates that this polymer includes 9 weight percent HDI, has an ATPS-6 soft segment and is not ionized. The polymer HMATPS-33-7.6 has been completely reacted with 1.3-propane sulfone and contains 7.6 weight percent 1,3-propane sulfone (or 5.0 weight percent $SO_3$).

TABLE I

MATERIAL CHARACTERIZATION

| SAMPLE | Composition (mole ratio) | Molecular Weight Mn | Mw | Hard Segment (wt. percent) |
|---|---|---|---|---|
| HMATPS-30A | ATPS-6/HDI/MDI/BD (2/1/2/1) | 33,000 | 90,000 | 30.1 |
| HMATPS-40 | ATPS-6/HDI/MDI/BD (2/1/3/2) | 33,000 | 90,000 | 40.4 |
| HMATPS-30B | ATPS-6/HDI/MDI/BD (3/2/3/2) | 32,000 | 108,000 | 30.3 |
| ATPS-50 | ATPS-6/MDI/BD (1/2/1) | 28,000 | 94,000 | 49.6 |
| HMATPS-9 | ATPS-6/HDI/BD (1/2/1) | 31,000 | 97,000 | 8.8 |
| HMATPS-31-0[b] | ATPS-6/HDI/MDI/MDEA (2/1/2/1) | 29,000 | 94,000 | 31.1 |
| HMATPS-33-3.9[b] | ATPS-6/HDI/MDI/MDEA/1,3PS (2/1/2/1/0.5) | 29,000 | 94,000 | 33.3 |
| HMATPS-35-7.6[b] | ATPS-6/HDI/MDI/MDEA/1,3PS (2/1/2/1/1) | 29,000 | 94,000 | 35.1 |
| HMATPS-29 | ATPS-6/HDI/MDI/ED | 38,000 | 91,000 | 29.0 |

TABLE I-continued

| | MATERIAL CHARACTERIZATION | | | |
|---|---|---|---|---|
| | Composition | Molecular Weight | | Hard Segment |
| SAMPLE | (mole ratio) | Mn | Mw | (wt. percent) |
| | (2/1/2/1) | | | |

[a]Equivalent polystyrene molecular weight determined by gel permeation chromatography (GPC).
[b]Weight percent of SO₃ added during synthesis.

C. Test Methods

Films of block copolymers were spin cast from 15 percent DMA solutions, dried in a vacuum oven at 60 degrees C. for 48 hours, and stored in a vacuum desiccator at room temperature. Film thickness was varied from 50 to 200 micrometers depending upon the particular requirements of the study.

Gel permeation chromatography studies were carried out by passing 0.5 percent DMA solutions of these polymers through a Beckman 114M pump equipped with a series of Altex micro-spherogel columns and a Altex 156 refractive index detector. The molecular weight calibration curve (logarithm of molecular weight as a function of retention volume) was obtained using a series of polystyrene standards dissolved in DMA having molecular weights from about 3,000 to about 230,000. The molecular weights of the present block copolymers were calculated from the calibration curve, and the results are listed in Table I.

Thermal analysis was conducted by recording differential scanning calorimetry (DSC) thermograms from −150 degrees C. to 230 degrees C. using a Perkin-Elmer DSC-2C interfaced with a model 3600 Data Station using standard TADS software. Temperature and enthalpy calibrations were carried out using indium and mercury standards. A heating rate of 20 degrees C. per minute under a helium gas purge was used on samples of 15±3 milligrams. The data processing software allowed automatic subtraction of the baseline, normalization of the thermogram for the sample weight and calculation of $T_g$ between specified limits.

Dynamic mechanical data were obtained using a Rheovibron DDV-IIC apparatus which was controlled by a LSL-11 microcomputer. All measurements were carried out under a nitrogen purge at a test frequency of 110 Hz and at a heating rate of about 2 degrees C. per minute.

Room temperature uniaxial stress-strain data were taken on a Instron table model device at a crosshead speed of 0.254 centimeters/minute. Dumbbell-shaped samples were stamped out with an ASTM D1708 standard die. Engineering stress data were calculated as the ratio of force to initial cross-section area. The stress-strain data reported are the average results from at least four measurements per sample.

Small angle x-ray scattering (SAXS) experiments were performed at the Stanford Synchrotron Radiation Laboratory (SSRL) using the SAXS camera at beam line 11-2. The scattering profiles were recorded with a one-dimensional position-sensitive proportional counter. The SAXS camera had a pin hole geometry with a sample to detector distance of 50 centimeters covering a scattering vector of q-range from 0.015 to 0.35 1/Å A (q=4πsinθ/λ), where 0 is half the observation angle and is the wavelength (1.47 Å). The data corrected for dark current, detector sensitivity, parasitic scattering and sample absorption are presented as relative intensity versus scattering vector q.

Standard scattering theories for two phase systems were used to analyze SAXS profiles [Glatter et al., Small Angle X-ray Scattering, Academic Press, New York (1982) and Guinier et al., Small Angle Scattering of X-ray, John Wiley and Sons, Inc., New York (1955)]. Assuming a constant electron density in each of two phases separated by a sharp interface, Porod's inhomogeneity length $1_p$ [Kahovec et al., Kolloid Z., Z. Polym., 133, 16 (1953)] was used to characterize the characteristic length pertaining to the morphology. Porod's inhomogeneity length is defined as $$1_p = 8\pi Q/K \quad (1)$$

where Q is the invariance of the scattering profile $$Q = \int_0^\infty I(q)q^2 dq = V(\Delta\rho)\phi_1\phi_2 2\pi^2 \quad (2)$$

and K is the Porod's constant [G. Porod, Kolloid Z., 124, 83 (1951)], and $$\lim_{q\to\infty} I(q) = K/q^4 + b \quad (3)$$

where b is the background scattering which is a constant in wavevector range considered.

II. Results and Discussion

A. Synthesis

It has been reported [Yilgor et al., Polymer, 25, 1800 (1984) and Yu et al., J. Polym. Sci. Polym. Phys. Ed., 23, 2319 (1985)] that the synthesis of polysiloxane-based polyurethanes suffers from the problem of selecting a suitable solvent due to the large difference in the solubility parameters of the components of the system.

According to the present invention, insertion of an organic diisocyanate into an amine-terminated polysiloxane improves the solubility of the oligomers in polar solvents such as DMA. The solvent (DMA) can be used for polymer synthesis and zwitterionization reactions without any evidence of phase separation in solution.

The molar ratios of hexane diisocyanate (HDI) to amine-terminated polysiloxane in the modified polysiloxane oligomer synthesis were 1:2 and 2:3. There is a distribution, however, on the molecular weight of the oligomer as the result of the condensation reaction. The number average molecular weights of the oligomers were 1410 and 2070, respectively.

B. Thermal Analysis

Figure 2:
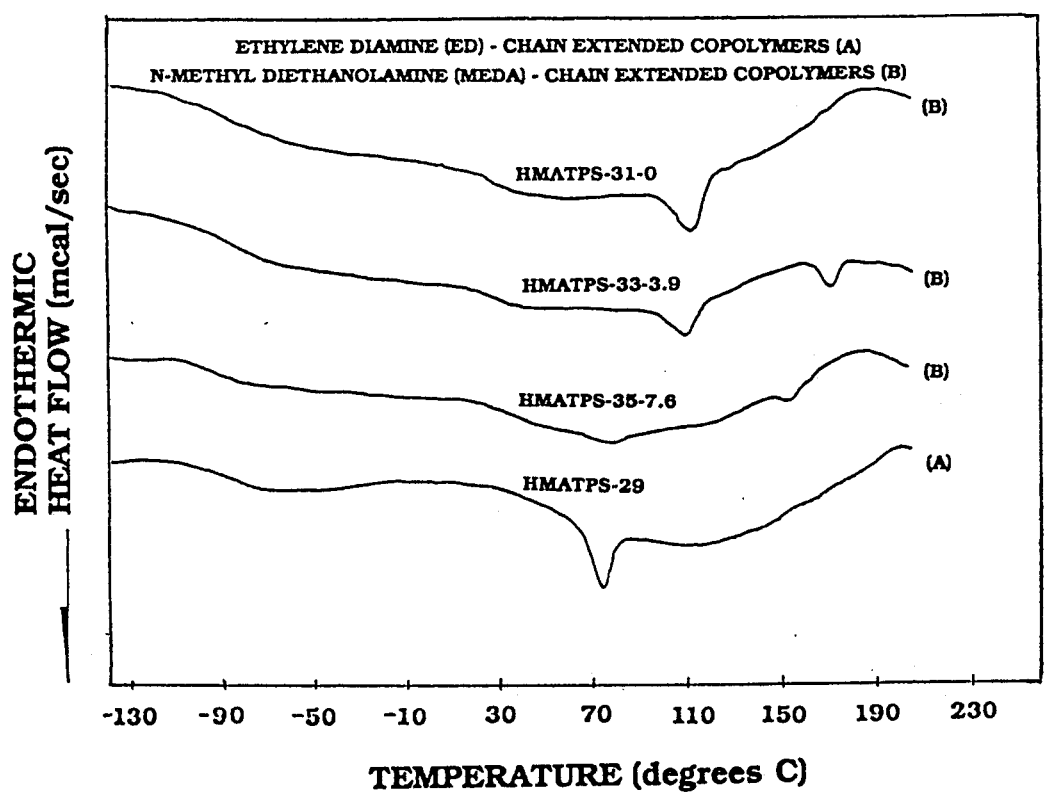
FIG. 2 illustrates DSC curves of the ethylene diamine (ED) and N-methyl diethanolamine (MDEA) chain extended materials. See the following discussion for sample code definitions.
Figure 3:
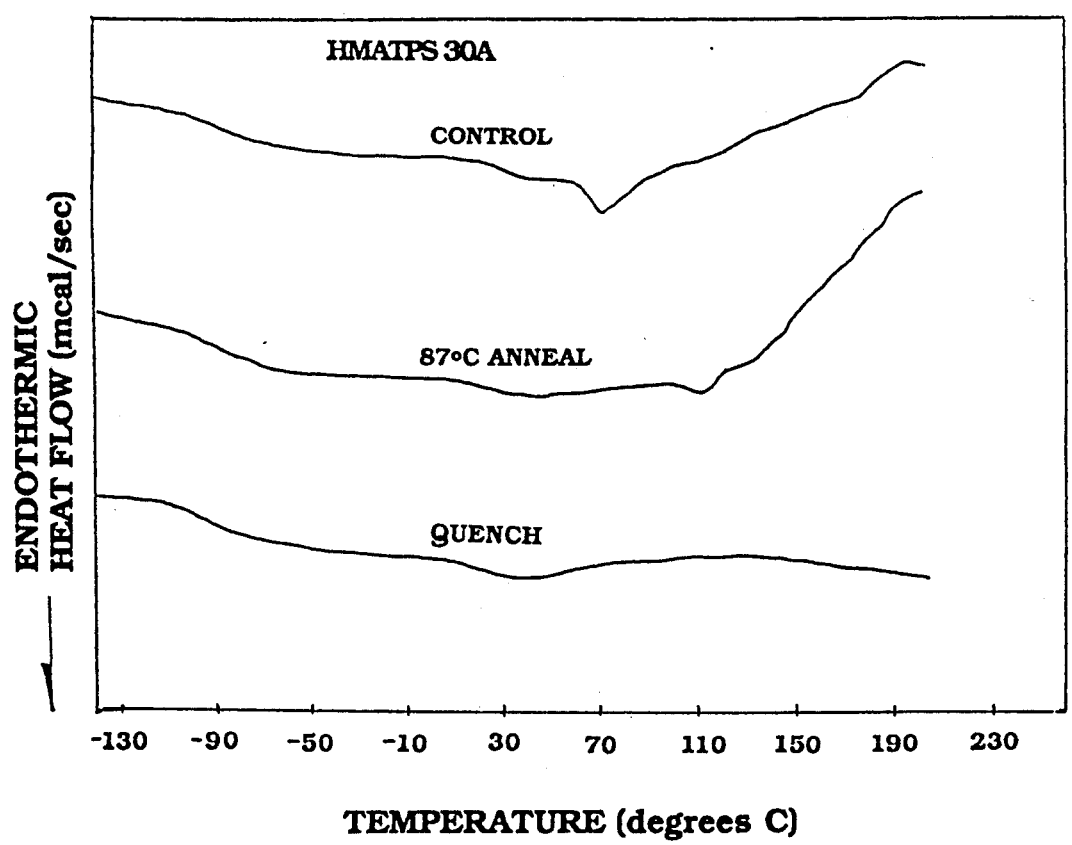
FIG. 3 illustrates DSC curves of annealed and quenched HMATPS-30A.

Differential scanning calorimetry (DSC) curves of representative HDI-modified PDMS polyurea urethanes and their corresponding ionomers are shown in FIGS. 1 to 3. The thermal transition data are provided in Table II.

TABLE II

DSC RESULTS

| SAMPLE | Composition (mole ratio) | $T_g$ (degrees C.) (1) | (2) | (3) |
|---|---|---|---|---|
| HMATPS-30A | ATPS-6/HDI/MDI/BD (2/1/2/1) | −90 | −92 | −91 |
| HMATPS-40 | ATPS-6/HDI/MDI/BD (2/1/3/2) | −98 | −95 | −87 |
| HMATPS-30B | ATPS-6/HDI/MDI/BD (3/2/3/2) | −89 | −97 | −89 |
| ATPS-50 | ATPS-6/MDI/BD (1/2/1) | −94 | −102 | |
| HMATPS-31-0 | ATPS-6/HDI/MDI/MDEA (2/1/2/1) | −87 | −91 | −87 |
| HMATPS-33-3.9 | ATPS-6/HDI/MDI/MDEA (2/1/2/1) 50 PERCENT SULFONATED | −89 | −93 | −90 |
| HMATPS-35-7.6 | ATPS-6/HDI/MDI/MDEA (2/1/2/1) 100 PERCENT SULFONATED | −93 | −96 | −94 |
| HMATPS-29 | ATPS-6/HDI/MDI/ED (2/1/2/1) | −97 | −94 | −97 |
| HMATPS | ATPS-6/HDI (2/1) | −95 | | |
| ATPS-6 | 100 PERCENT POLYSILOXANE OLIGOMER | −116 | | |

(1) Solvent cast samples.
(2) Samples annealed at 87 degrees C. for 12 hours.
(3) Samples quenched from 210 degrees Celcius to −140 degrees C. at 160 degrees C. per minute.

The DSC data show that the glass transition temperature of the HDI-modified PDMS oligomer designated HMATPS (−95 degrees C.) is 21 degrees C. higher than that of the pure ATPS-6 oligomer (−116 degrees C.). There are at least two factors that can cause an increase in oligomer $T_g$. First, the urea linkages in HMATPS oligomers are capable of forming interurethane hydrogen bonds which restrict the molecular motion of the oligomer. The second factor is the molecular weight dependence of the oligomer $T_g$ which tends to increase with an increase in molecular weight. The $T_g$s of the HDI-modified soft segments in the segmented polyurea urethane materials are 2 to 8 degrees C. higher than that of the HMATPS oligomer. It is also observed that the soft segment $T_g$ decreases with increasing hard segment content or degree of ionization in these materials. An increase in either hard segment content or degree of ionization leads to improved hard domain cohesion and an increase in the extent of phase separation.

A DSC curve of a segmented polyurethane based on a 2000 molecular weight hydroxyl-terminated polydimethylsiloxane soft segment and 31 weight percent MDI-BD hard segments is shown in FIG. 1. The HTPS-based polyurethane shows a lower soft segment $T_g$ and a higher hard segment crystallinity as compared to HMATPS-30B. It is possible that the higher degree of phase mixing which raises the $T_g$ is a direct result of the insertion of HDI into the PDMS soft segments since the urea linkage in the soft segment is capable of forming intersegmental hydrogen bonding with the hard segments. The polarity of the soft segment is also raised due to the urea group incorporation in the PDMS backbone. This can also raise the $T_g$. HMATPS-30A and HMATPS-30B have identical hard segment contents but the soft segment molecular weights are 1410 in the HMATPS-30A and 2070 in the HMATPS-30B, respectively. These two materials exhibit similar thermal properties. Since the sample with longer soft segments also contains more urea groups per soft segment, the effect of higher soft segment molecular weight leading to a higher degree of phase separation may be offset by the intersegmental hydrogen bonding which promotes phase mixing.

The DSC data in Table II show that the soft segment glass transition temperature varies with the type of chain extender used in these materials. MDEA and ED chain extended materials exhibit higher and lower soft segment $T_g$s, respectively, than BD chain extended samples. The hard blocks in the ED chain extended material include urea linkages which have a higher intrasegmental hydrogen bonding capability. Block copolymers containing urea hard blocks tend to exhibit a higher degree of phase separation than those containing urethane hard blocks. If there are fewer hard segments mixed in the soft domain due to a higher degree of phase separation, the soft segment $T_g$ will be lower. The higher soft segment $T_g$s found in MDEA chain extended materials are due to the difficulty of the hard segments to align and crystallize which results in an increase in phase mixing.

Zwitterionization effectively increases the extent of phase separation in segmented polyurethanes as indicated by lower soft segment $T_g$s which are reported in studies of polyether polyurethanes. Hwang et al., *Polym. Engr. and Sci.*, 21, 1027 (1981) and Yang et al., *Makromol. Chiem.*, 184, 651 (1983). In this study, a similar conclusion can be reached as the ionized materials exhibited lower soft segment $T_g$s.

FIG. 3 shows DSC curves measured after a fast quench from 210 degrees C. to −140 degrees C. DSC thermograms of samples annealed at 87 degrees C. are also included in that Figure. The quenching process does not effect the soft segment glass transition temperature but annealing does decrease the soft segment $T_g$. This may be because the isolated hard segments originally in the soft segment phase settle into the hard segment microdomains during the annealing process.

All materials studied in this investigation exhibit small endotherms in the temperature range from 60 degrees C. to 160 degrees C. These endotherms are shifted to higher temperature by annealing and disappear in quenched samples. These endotherms can be attributed to the dissociation of short range order in the hard segment microdomains.

C. Dynamic Mechanical Analysis

Figure 4:
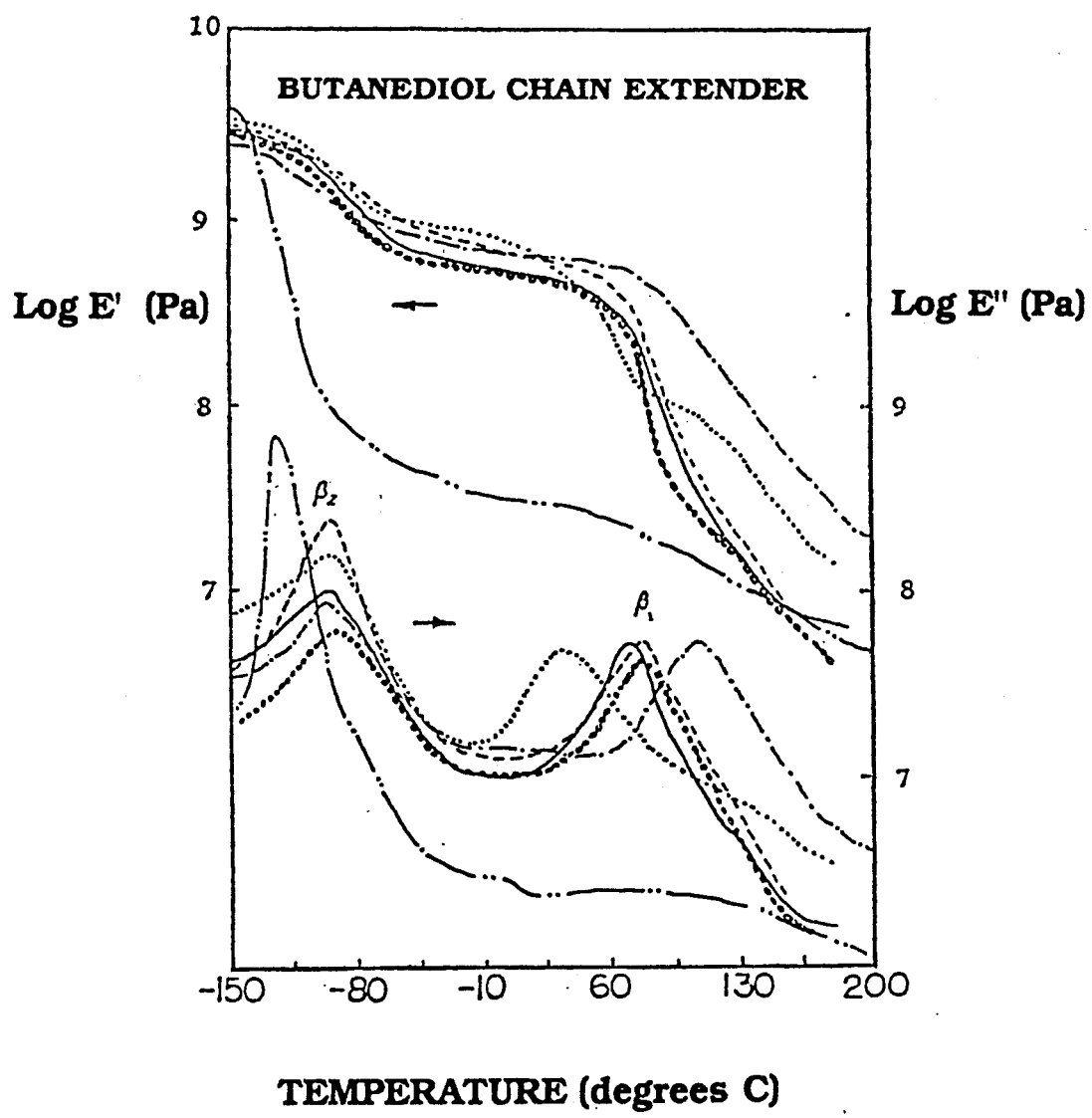
FIG. 4 illustrates storage modulus E' and loss modulus E" curves of the butanediol chain extended materials. ( ·········· HMATPS-9, —·—·— ATPS-50, — — — — — — — — — HMATPS-40, ∘∘∘∘∘∘∘∘∘∘ HMATPS-30A, ——————— HMATPS-30B, —··—··— HTPS-31).
Figure 5:
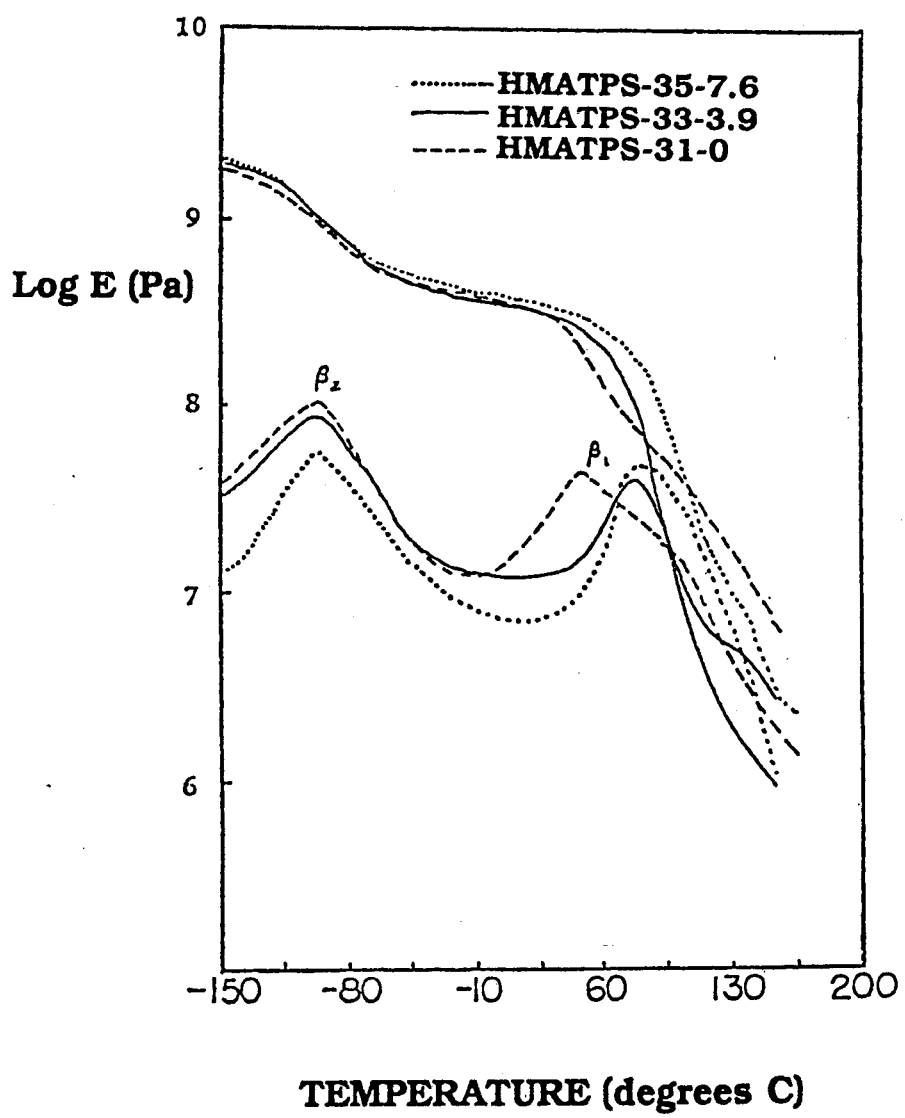
FIG. 5 illustrates storage modulus E' and loss modulus E" curves of the materials with different chain extenders.
Figure 6:
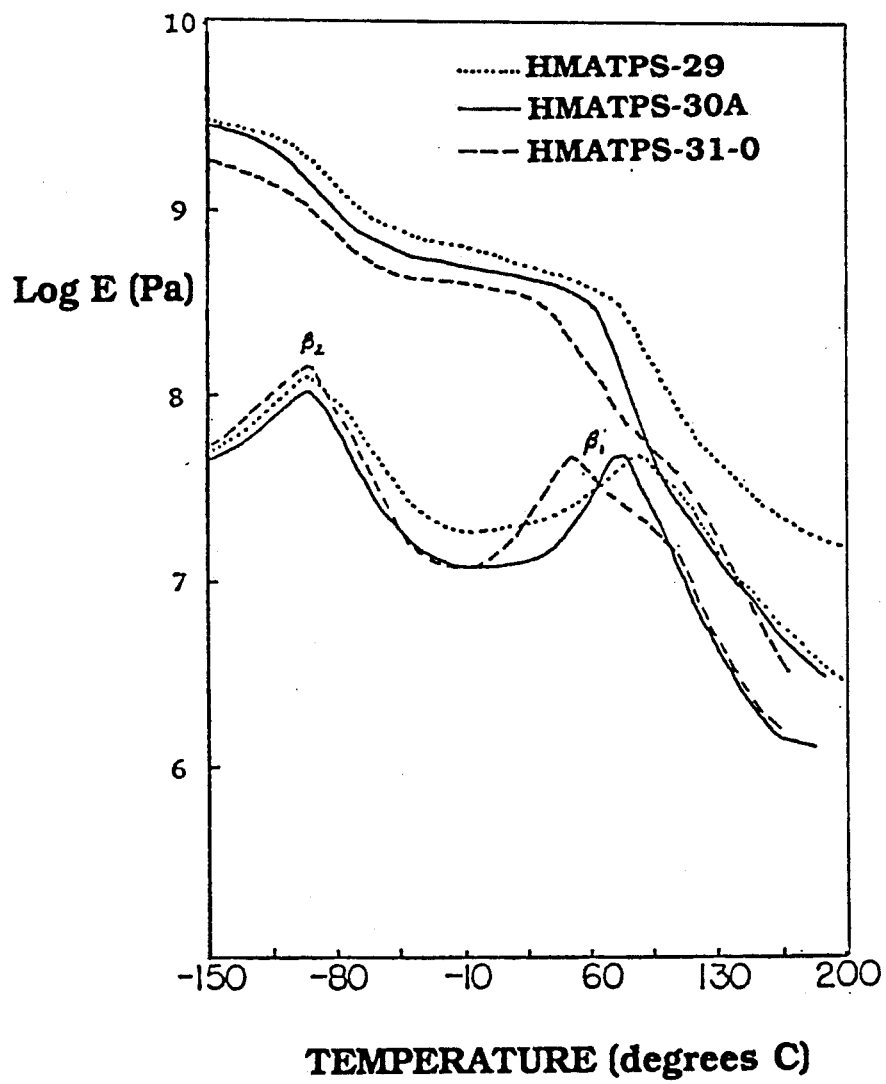
FIG. 6 illustrates storage modulus E' and loss modulus E" curves of the materials with different levels of ionization.

The results of dynamic mechanical testing are presented in FIGS. 4–6 and in Table III.

TABLE III
DYNAMIC MECHANICAL RESULTS

| SAMPLE | $\beta_2$ max. (°C.) | $\beta_1$ max. (°C.) | Plateau Region | | |
|---|---|---|---|---|---|
| | | | onset (°C.) | end (°C.) | width (°C.) |
| HMATPS-30A | −98 | 65 | −66 | 58 | 124 |
| HMATPS-40 | −100 | 68 | −66 | 64 | 130 |
| HMATPS-30B | −98 | 66 | −67 | 58 | 125 |
| ATPS-50 | −102 | 94 | −69 | 69 | 138 |
| HMATPS-31-0 | −97 | 43 | −66 | 26 | 92 |
| HMATPS-33-3.9 | −99 | 68 | −69 | 58 | 127 |
| HMATPS-35-7.6 | −101 | 75 | −71 | 66 | 137 |
| HMATPS-29 | −101 | 75 | −66 | 64 | 130 |
| ATPS-6 | −101 | 24 | −71 | 25 | 96 |

In accordance with the DSC data, the $\beta_2$ peak of the loss modulus E″ curves, which is attributed to the glass transition of the soft segments, shifts several degrees in different materials. Greater changes are observable in the hard segment $T_g$ measured by the $\beta_1$ peak on the E″ curves. An important characteristic found in these segmented polyurethanes is that they exhibit high values of rubbery plateau modulus considering their relatively low hard segment contents. This observation may be attributed to some degree of phase mixing and a higher degree interdomain interconnectively achieved in the morphological structure of these materials.

FIG. 4 illustrates the effects of soft segment structure and molecular weight on the dynamic mechanical spectra of those materials based on the butanediol chain extender. The hard segment glass transition is reflected by the $\beta_1$ peaks in the loss modulus curves at higher temperatures. The hard segment $T_g$ is governed by the hard segment structure, crystallinity, as well as the level of phase mixing within the hard segment microdomains. The two extremes of hard segment $T_g$s are HMATPS-9 with a hard segment $T_g$ at 24 degrees C. and ATPS-50 with the $T_g$ shifted to 94 degrees C. Since the hard segments in HMATPS-9 are HDI-BD, it is expected that the lower hard segment $T_g$ results from the increased flexibility of HDI-BD as compared to MDI-BD hard segments. The hard segment glass transition temperatures of HMATPS-30A, HMAPTS-30B, and HMATPS-40 are observed between 65 degrees C. to 68 degrees C. From the values of $\beta_1$ peak position listed in the Table III, it is observed that the hard domain cohesion increases slightly with an increase in hard segment content while the soft segment glass transition temperature decreases slightly.

FIG. 4 also shows a striking difference in dynamic mechanical properties between the materials based on HDI-modified polydimethylsiloxane and pure PDMS soft segments at a comparable hard segment content. The tensile test results also indicate that much higher Young's moduli were observed in the HDI-modified PDMS-based polyurethanes compared to the pure PDMS polyurethanes.

Such unusually high rubbery plateau moduli and room temperature tensile moduli can be attributed to several factors unique to this system. First, the level of phase mixing is raised due to an increased degree of intersegmental hydrogen bonding as the result of incorporation of HDI units into the PDMS soft segments. The phase mixing may also involve a small amount of soft segment dissolved in the hard segment microdomain which increases the hard segment domain volume fraction. Phase mixing in both the hard and soft microdomains can lead to a higher rubbery plateau modulus in this system.

Second, the HDI units can also be bonded to the surfaces of the urethane hard segment microdomains and increase the interdomain interfacial adhesion. This causes a decrease in the effective soft segment length between two hard segment domains is shorter. In addition, several HDI may associate with each other. The number of HDI units in such 'clusters' may be small enough so that they are not detected as an additional phase. However, these 'clusters' might act as crosslinks to raise the modulus of this system.

Finally, a higher level of interconnectivity between hard segment microdomains caused by phase mixing may lead to the presence of a more effective bicontinuous network morphology in this system.

All of the foregoing factors would tend to raise the rubbery plateau modulus in a two phase elastomer containing rigid and flexible phases. Since the hard segment glass transition temperature in this system tends to be lower, the association of HDI units in the hard segment phase may occur. However, it is difficult to distinguish whether intersegmental mixing occurs within the domains or at the domain interface. Due to the lack of direct methods to view the morphology, it is also difficult to distinguish whether a high hard segment domain volume fraction or a higher interconnectivity is the major contributor to the high modulus observed. The lower hard segment $T_g$ caused by the phase mixing in this system, however, implies a narrower temperature range for elastomeric behavior.

The dynamic mechanical spectra of HDI-modified PDMS polyurethanes containing different hard segments are shown in FIG. 5. The higher hard segment glass transition temperature in the ethylene diamine chain extended material (HMATPS-29) reflects the higher rigidity of urea hard segments. MDI-MDEA urethane hard segments in material HMATPS-31-0 are not crystallizable due to the branched structure of MDEA. Thus, this sample has the lowest hard segment $T_g$ and storage modulus among all materials studied.

FIG. 6 illustrates the effects of level of zwitterionization on the MDEA chain extended materials. The soft segment $T_g$ drops slightly as the level of ionization increases. The hard segment $T_g$, observed from the peak on the loss modulus curve, is shifted to a higher temperature as a result of the improvement of hard domain cohesion accomplished at a higher level of zwitterionization.

D. Tensile Properties

Figure 7:
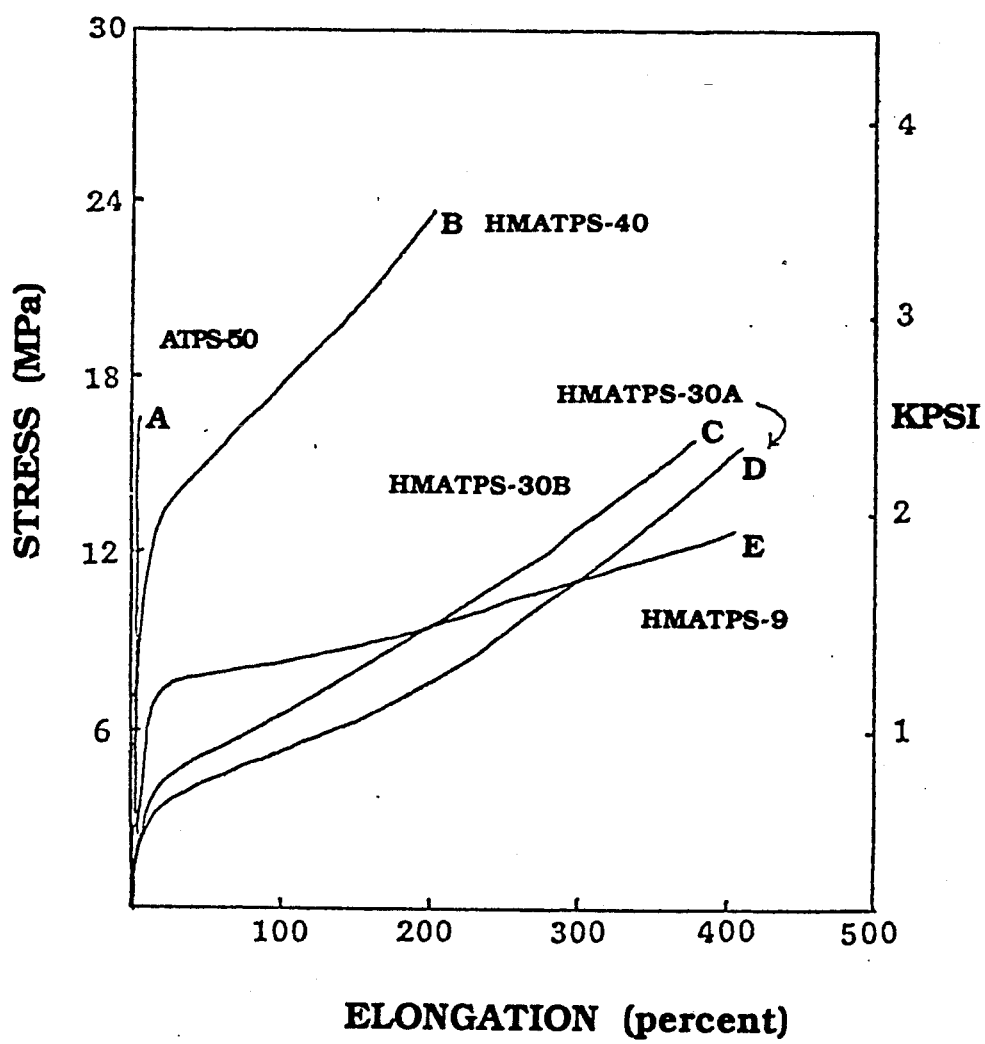
FIG. 7 illustrates stress-strain curves of the butanediol chain extended materials (A: ATPS-50, B: HMATPS-40, C: HMATPS-30B, D: HMATPS-30A, E: HMATPS-9).
Figure 8:
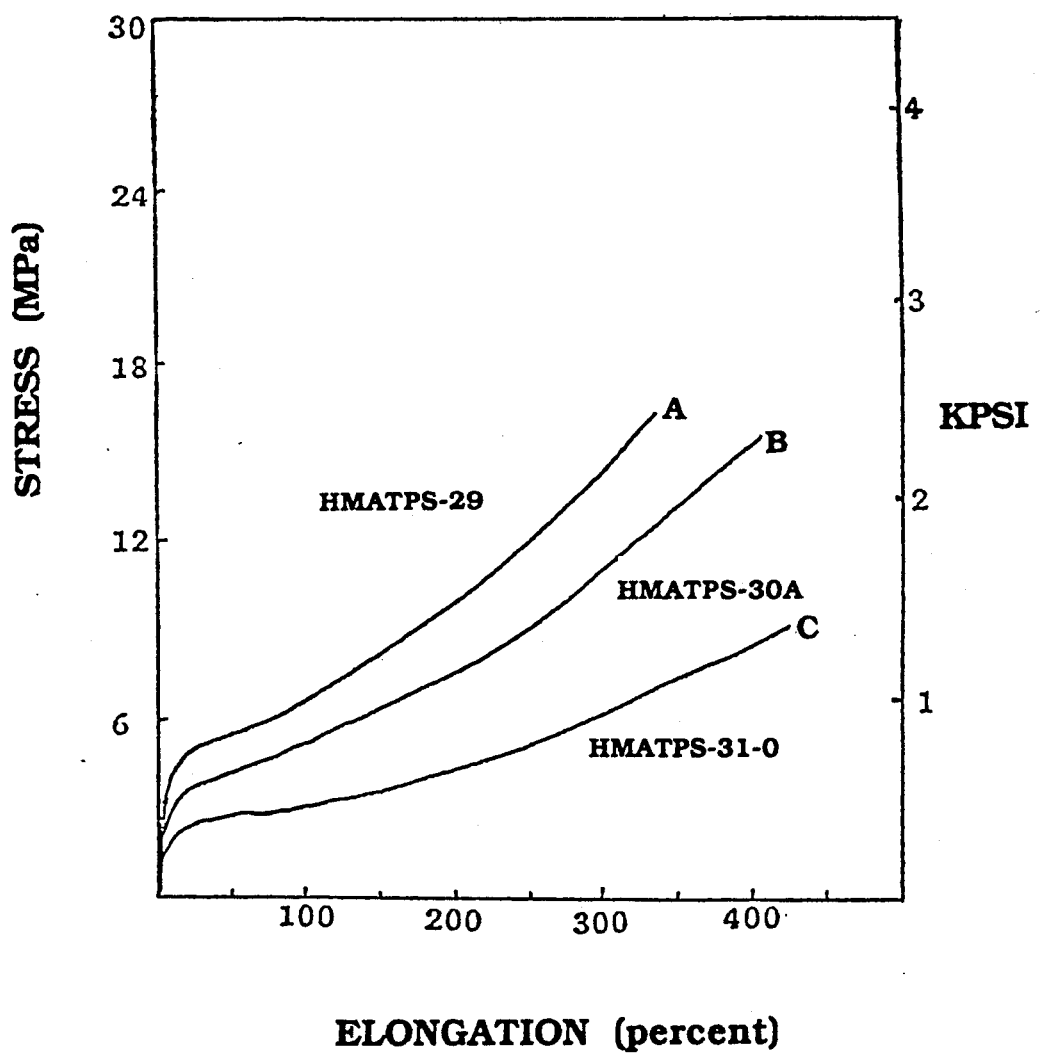
FIG. 8 illustrates stress-strain curves of the materials with different chain extenders (A: HMATPS-29, B: HMATPS-30A, C: HMATPS-31-0).
Figure 9:
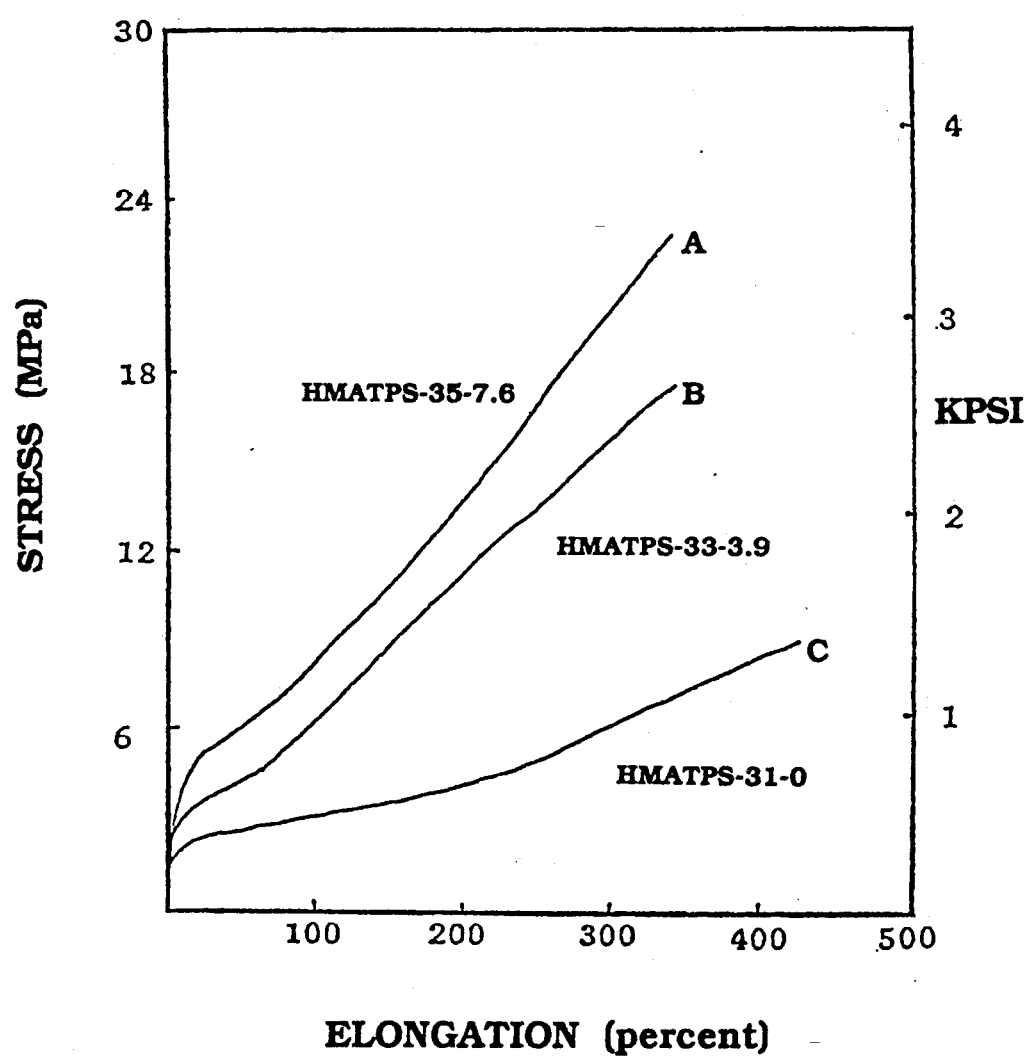
FIG. 9 illustrates stress-strain curves of the materials with different levels of ionization. (A: HMATPS-35-7.6, B: HMATPS-33-3.9, C: HMATPS-31-0).

The engineering stress-strain curves of the segmented polyurethane materials are shown in FIGS. 7–9. Table IV summarizes the tensile properties. These materials exhibit improved tensile properties compared to the materials containing pure polydimethylsiloxane soft segments studied previously. Yu et al., *J. Polym. Sci., Poly. Phys. Ed.*, 23, 2319 (1985).

TABLE IV

TENSILE PROPERTIES

| SAMPLE | Young's Modulus (MPa) | Ultimate Stress (MPa) | Elongation at Break (percent) |
|---|---|---|---|
| HMATPS-30A | 42.7 | 15.4 | 407 |
| HMATPS-40 | 175.0 | 23.8 | 203 |
| HMATPS-30B | 41.3 | 15.4 | 377 |
| ATPS-50 | 378.0 | 16.8 | 4 |
| HMATPS-31-0 | 31.0 | 9.1 | 426 |
| HMATPS-33-3.9 | 44.8 | 17.5 | 340 |
| HMATPS-35-7.6 | 56.7 | 22.4 | 335 |
| HMATPS-29 | 61.6 | 16.1 | 332 |

The higher hard segment content in the BD chain extended materials leads to higher Young's modulus and ultimate stress but lower elongation at break. These observations agree with the general trends found in many two phase polyurethane systems and may be attributed to changes in the volume fraction of the hard domains. The materials having similar hard segment content but different soft segment molecular weights possess similar tensile properties.

The higher tensile strength of the EDA chain extended materials may be attributed to their higher hard domain cohesion. The lower ultimate stress and higher elongation at break of the MDEA chain extended material result from their higher degree of phase mixing and lower hard domain cohesion. Ionic aggregation in the hard domains increases the hard domain cohesion and raises the tensile strength and modulus of those materials.

E. Small Angle X-ray Scattering

Figure 10:
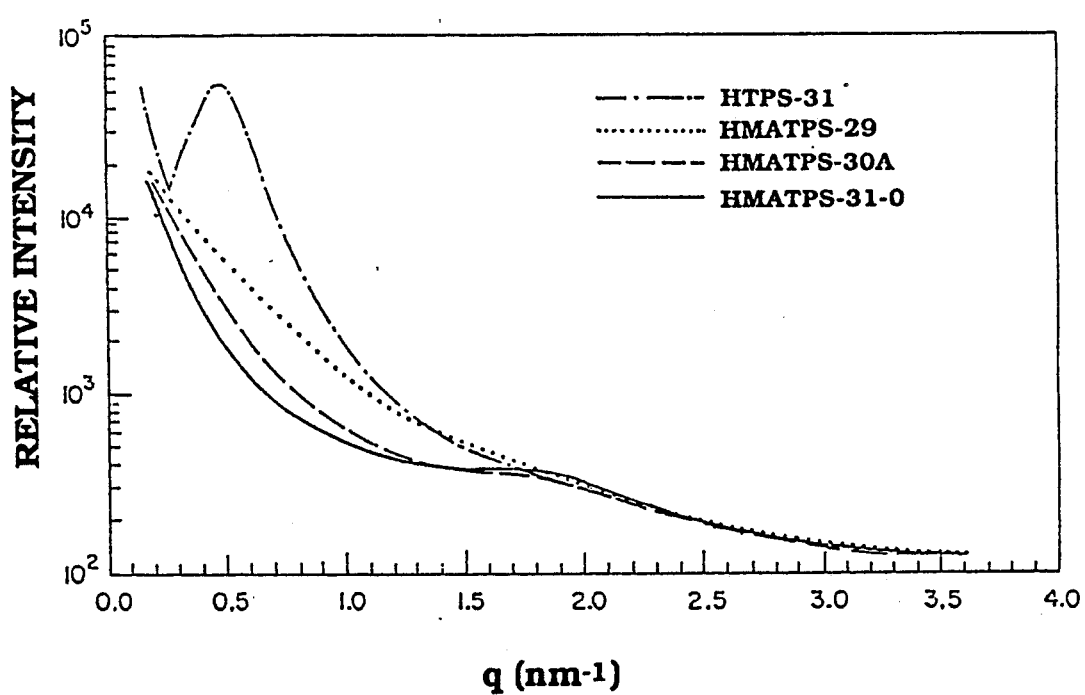
FIG. 10 illustrates small angle x-ray scattering profiles for materials with different chain extenders.
Figure 11:
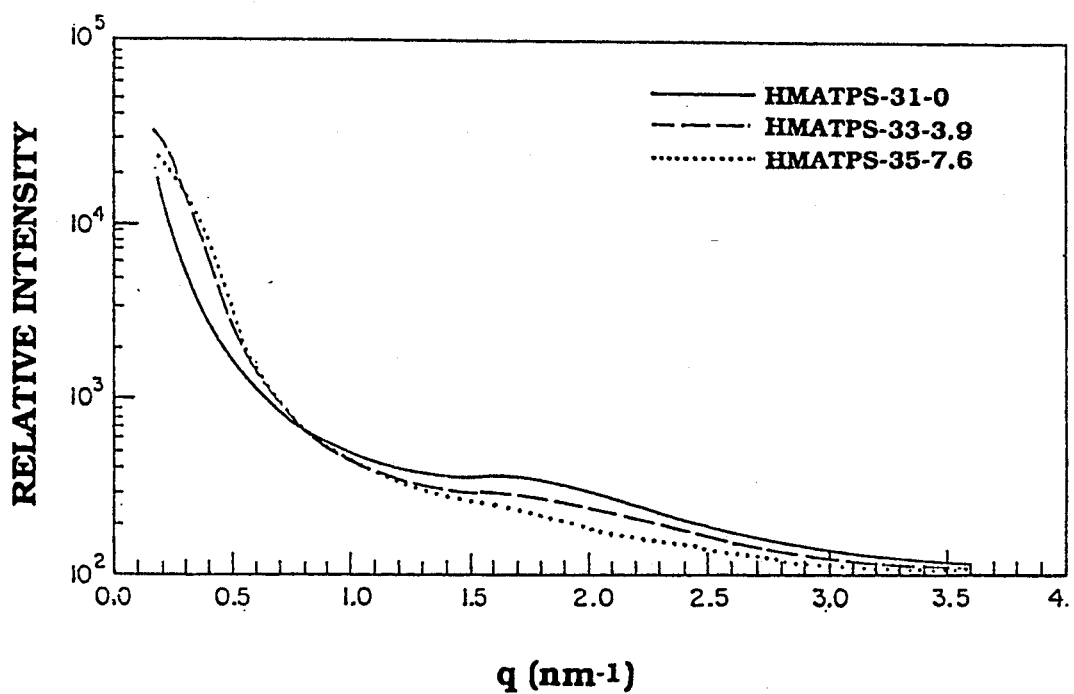
FIG. 11 illustrates small angle x-ray scattering profiles for materials with different levels of ionization.

FIG. 10 shows the SAXS curves of the polymer systems containing different chain extenders. SAXS profiles of the MDEA chain extended materials and their ionomer derivatives are presented in FIG. 11. These scattering profiles show the typical scattering profile of the materials of this invention.

In FIG. 10, there is a striking difference in the SAXS profile between the HTPS-based materials and the HMATPS based materials with comparable hard segment content. The well distinguished SAXS peak of the HTPS materials may be attributed to their high degree of phase separation. For the HMATPS materials, the HDI units incorporated in the soft segment may enhance phase mixing and create a finer textured interconnected hard phase morphology. This alternation in morphology might explain both their unusually high modulus and the lack of a SAXS peak in their scattering profiles.

By changing chain extenders, there is a significant change in the SAXS curves. The EDA chain extended materials have a higher scattering power than the BD and MDEA extended materials. Ionization increases the scattering intensity at lower angles while the intensity at higher angle decreases. These changes in the scattering curves indicate that the degree of phase separation and domain dimensions may be different in these materials.

Figure 12:
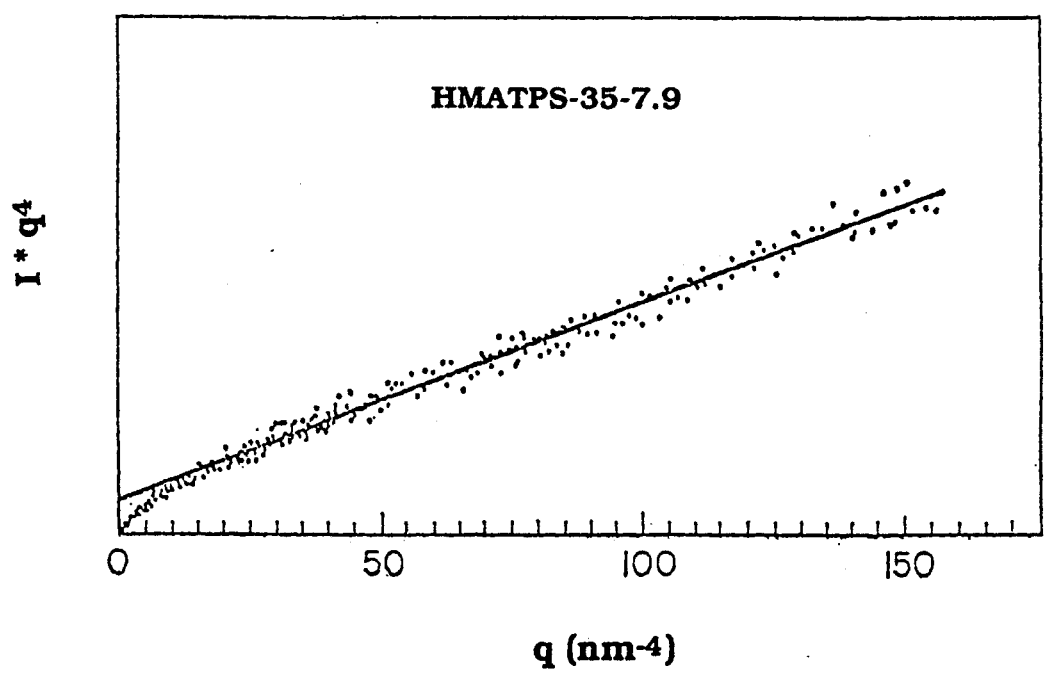
FIG. 12 is a Porod's law plot for sample HMATPS-35-7.6.

Inhomogeneity lengths and invariant calculations have been determined for these data in order to derive structural information. FIG. 12 shows a typical example of a plot to determine Porod's constant. The extended linear region in the plot of $Iq^4$ vs. $q^4$ is used to determine the constant. The inhomogeneity length and the invariant of the scattering profiles estimated using equation 1 and 2 are listed in Table V.

TABLE V

SAXS RESULTS

| SAMPLE | Invariant | lp (Å) |
|---|---|---|
| HMATPS-31-0 | 1.000 | 9.9 |
| HMATPS-33-3.9 | 1.135 | 16.5 |
| HMATPS-35-7.6 | 1.171 | 27.0 |
| HMATPS-30A | 1.273 | 13.6 |
| HMATPS-40 | 2.496 | 14.6 |
| ATPS-50 | 2.752 | 12.5 |
| HMATPS-29 | 1.512 | 17.2 |

(1) The invariant has been normalized with respect to sample HMATPS-31-0.
(2) lp is Porod's inhomogeneity length defined by equation (1) in the specification.

Equation 2 indicates that, with $\phi_1 > \phi_2$, an increase of invariant can be due to an increase in $\phi_1$ or $\Delta\rho$. In the MDEA chain extended materials of similar hard segment content, increasing the degree of ionization slightly increases the invariant. This was most likely caused by an improvement of phase separation which increases the purity of each phase which raises both $\phi_1$ and $\Delta\rho$. A similar effect is also observed when the chain extender is varied. The invariant calculation suggests that the degree of phase separation decrease in the order EDA > BD > MDEA.

$T_g$ has been used as an indication of the degree of phase separation in polyurethane systems [Schneider et al., J. Macromol. Sci. Phys., B11, 527 (1975)]. If materials with similar hard segment content and the same soft segment composition have the same soft segment $T_g$, one may assume that these materials have similar extents of phase separation. Tables II and III show that varying the ionization level affects $T_g$ in a similar fashion as varying the type of chain extender. In general, at roughly the same hard segment content, the change in invariant parallels the change in $T_g$.

An improvement in the degree of phase separation will tend to increase the domain size. Thus, the changes in Porod's inhomogeneity length, $l_p$, caused by changing the chain extender are consistent with the changes in the degree of phase separation. The much larger increase in Porod's inhomogeneity length caused by increasing the ionization level compared to that caused by varying the chain extender suggests a significant thickening of the hard domain through ionization. Comparing the $l_p$, Young's modulus and the ultimate properties of the EDA chain extended sample with those of the 100 percent ionized MDEA chain extended sample, the smaller $l_p$ in the EDA extended sample suggests that the morphology of EDA extended sample might be composed of a thinner and more interconnected hard domain providing a higher modulus for this material.

Increasing the hard segment content in the BD chain extended materials increases the invariant, which is a direct consequence of increasing the hard domain volume fraction over the range of hard segment content studied. The $l_p$ of these materials does not show much variation which suggests that the hard domain thickness is not significantly affected by hard segment content.

As demonstrated herein, the incorporation of organic diisocyanate units in the polysiloxane soft segments significantly changes the morphology and physical properties of the resulting copolymers. The extent of phase mixing in these segmented block copolymers is increased as a result of improved segmental compatibility. The hard segment glass transition temperatures decrease as a result of dissolved diisocyanate units in the hard segment microdomains in this system as compared with the copolymers containing pure PDMS soft segments.

Moreover, the introduction of crystallinity or ionic functionality enhances the hard segment aggregation and raises the level of phase separation slightly. Increased hard domain volume fraction and interconnectivity as results of phase mixing in this system lead to a high rubbery plateau modulus.

Thus, the incorporation of diisocyanate units into the polysiloxane soft segments substantially improves the tensile properties of these segmented polyurethanes.

While the present invention has been described with reference to particular embodiments, it will be understood that various changes and modifications can be made without departing from the spirit of the invention.

What is claimed is:

1. A polysiloxane-containing block copolymer based on:
   (a) an oligomer comprising the reaction product of
      (i) a linear aliphatic diisocyanate; and
      (ii) a molar excess relative to said aliphatic diisocyanate of a polysiloxane represented by the formula:

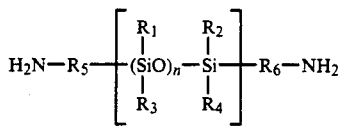

wherein
   n is an integer from 1 to about 200,
   $R_1$, $R_2$, $R_3$ and $R_4$ are each independently selected monovalent linear, branched or cyclic aliphatic or aromatic hydrocarbon radicals, including substituted or unsubstituted hydrocarbon radicals, containing from 1 to about 16 carbon atoms each, and
   $R_5$ and $R_6$ are independently selected divalent linear branched or cyclic aliphatic or aromatic hydrocarbon radicals, including substituted or unsubstituted hydrocarbon radicals, containing from 1 to about 16 carbon atoms each;
   (b) an organic diisocyanate; and
   (c) an independently selected $C_2$–$C_{20}$ alkyl diol, $C_2$–$C_{20}$ aryl diol, $C_2$–$C_{20}$ alkyl diamine or $C_2$–$C_{20}$ aryl diamine.

2. The block copolymer according to claim 1 wherein the mole ratio of the aliphatic diisocyanate to the polysiloxane in the oligomer is from about 1:2 to about 4:5.

3. The block copolymer according to claim 1 wherein the mole ratio of the aliphatic diisocyanate to the polysiloxane in the oligomer is about 1:2.

4. The block copolymer according to claim 1 wherein the mole ratio of the aliphatic diisocyanate to the polysiloxane in the oligomer is about 2:3.

5. The block copolymer according to claim 1 wherein the organic diisocyanate includes an alkylene group having from about 4 to about 20 carbon atoms each.

6. The block copolymer according to claim 5 wherein the second organic diisocyanate contains an arylene group having from about 4 to about 20 carbon atoms.

7. The block copolymer according to claim 1 wherein the organic diisocyanate is selected from the group consisting of 2,4-toluene diisocyanatae, 2,6-toluene diisocyanate, methylene bis (p-phenyl isocyanate), 1,5-naphthalene diisocyanate, methylene bis(p-cyclohexyl isocyanate), 1,6-hexane diisocyanate, isophorone diisocyanate, cyclohexyl diisocyanate and mixtures thereof.

8. The block copolymer according to claim 7 wherein the first organic diisocyanate is 1,6-hexane diisocyanate.

9. The block copolymer according to claim 1 wherein $R_1$, $R_2$, $R_3$ and $R_4$ are independently each selected from methyl, ethyl, propyl, butyl, isobutyl, pentyl, hexyl, vinyl, allyl, butenyl, hexenyl, cyclohexyl, cyclohexenyl or phenyl groups and $R_5$ and $R_6$ are independently selected from divalent radicals thereof.

10. The block copolymer according to claim 1 wherein at least one of the hydrocarbon radicals defined by $R_1$, $R_2$, $R_3$, $R_4$, $R_5$ and $R_6$ is halo-substituted or cyano-substituted.

11. The block copolymer according to claim 1 wherein $R_1$, $R_2$, $R_3$ and $R_4$ are each a methyl group.

12. The block copolymer according to claim 1 wherein $R_5$ and $R_6$ are each a propylene group.

13. The block copolymer according to claim 1 wherein the diol is selected from the group consisting of 1,4-butanediol, ethylene glycol, hexanediol, and mixtures thereof.

14. The block copolymer according to claim 1 wherein the diamine is selected from the group consisting of ethylene diamine, hexamethylene diamine, a 4-aminobenzylamine, 4,4'-diaminodicyclohexyl methane, a phenylene diamine, a toluene diamine, 4,4'-methylene bis(2-chloroaniline), 4,4'-diaminodiphenyl sulfone, 4,4'-diaminodiphenyl ether and mixtures thereof.

15. The block copolymer according to claim 1 wherein at least a portion of the urethane hydrogen atoms of the copolymer are replaced with lower alkyl ($C_1$–$C_6$) sulfonate groups.

16. The block copolymer according to claim 1 wherein the mole ratio of the oligomer to the organic diisocyanate to the diol or diamine is from about 2:1:1 to about 20:19:1.

17. The block copolymer according to claim 1 wherein the mole ratio of the oligomer to the organic diisocyanate to the diol or diamine is from about 2:1:1 to about 8:7:1.

18. A biocompatible medical device having at least one surface comprising the copolymer of claim 1.

19. A biocompatible medical device comprising the copolymer of claim 1.

20. A method for the production of a polysiloxane-containing polyurea urethane or polyurea block copolymer comprising:
   (a) providing an oligomer that comprises the reaction product of:
      (1) a linear aliphatic diisocyanate; and
      (2) a molar excess relative to said diisocyanate of a polysiloxane represented by the formula:

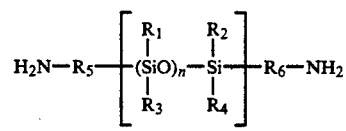

wherein
   n is an integer from 1 to about 200,
   $R_1$, $R_2$, $R_3$ and $R_4$ are each independently selected monovalent linear, branched or cyclic aliphatic or aromatic hydrocarbon radicals, including substituted or unsubstituted hydrocarbon radicals, containing from 1 to about 16 carbon atoms each, and
R₅ and R₆ are independently selected divalent linear branched or cyclic aliphatic or aromatic hydrocarbon radicals, including substituted or unsubstituted hydrocarbon radicals, containing from 1 to about 16 carbon atoms each;

(b) admixing an organic diisocyanate with the oligomer of (a); and (c) admixing an independently selected $C_2$–$C_{20}$ alkyl diol, $C_2$–$C_{20}$ aryl diol, $C_2$–$C_{20}$ alkyl diamine or $C_2$–$C_{20}$ aryl diamine with the mixture of (b).

21. The method according to claim 20 wherein the organic diisocyanate includes an alkylene group having from about 4 to about 20 carbon atoms each.

22. The method according to claim 21 wherein the second organic diisocyanate contains an arylene group having about 4 to about 20 carbon atoms.

23. The method according to claim 20 wherein the organic diisocyanate is selected from the group consisting of 2,4-toluene diisocyanate, 2,6-toluene diisocyanate, methylene bis(p-phenyl isocyanate), 1,5-naphthalene diisocyanate, methylene bis(p-cyclohexyl isocyanate), 1,6-hexane diisocyanate, isophorone diisocyanate, cyclohexyl diisocyanate and mixtures thereof.

24. The method according to claim 23 wherein the aliphatic diisocyanate is 1,6-hexane diisocyanate.

25. The method according to claim 20 wherein $R_1$, $R_2$, $R_3$ and $R_4$ are each independently selected from methyl, ethyl, propyl, butyl, isobutyl, pentyl, hexyl, vinyl, allyl, butenyl, hexenyl, cyclohexyl, cyclohexenyl or phenyl groups and $R_5$ and $R_6$ are independently selected from divalent radicals thereof.

26. The method according to claim 10 wherein at least one of the hydrocarbon radicals defined by $R_1$, $R_2$, $R_3$, $R_4$, $R_5$ and $R_6$ is halo-substituted or cyano-substituted.

27. The method according to claim 20 wherein $R_1$, $R_2$, $R_3$, and $R_4$ are each a methyl group.

28. The method according to claim 20 wherein $R_5$ and $R_6$ are each a propylene group.

29. The method according to claim 10 wherein the diol is selected from the group consisting of 1,4-butanediol, ethylene glycol, hexanediol and mixtures thereof.

30. The method according to claim 10 wherein the diamine is selected from the group consisting of ethylene diamine, hexamethylene diamine, a 4-aminobenzylamine, 4,4'-diaminodicyclohexyl methane, a phenylene diamine, a toluene diamine, 4,4'-methylene bis (2-chloroaniline), 4,4'-diaminodiphenyl sulfone, 4,4'-diamino diphenyl ether or mixtures thereof.

31. The method according to claim 10 further including the step of replacing at least a portion of the urethane hydrogen atoms of the copolymer with lower alkyl ($C_1$–$C_6$) sulfonate groups.

32. A block copolymer prepared according to the method of claim 20.

33. An oligomer comprising the reaction product of:
(a) an organic linear aliphatic diisocyanate; and
(b) a molar excess relative to said aliphatic diisocyanate of a polysiloxane represented by the formula:

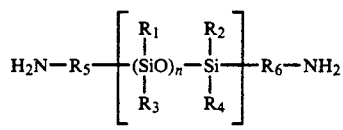

wherein
n is an integer from 1 to about 200;
$R_1$, $R_2$, $R_3$ and $R_4$ are independently each selected from linear, branched or cyclic aliphatic or aromatic hydrocarbon radicals, including substituted or unsubstituted hydrocarbon radicals, containing from 1 to about 8 carbon atoms each; and
$R_5$ and $R_6$ are independently selected from linear, branched or cyclic aliphatic or aromatic hydrocarbon radicals, including substituted or unsubstituted hydrocarbon radicals, containing from 1 to about 16 carbon atoms.

34. The block copolymer according to claim 1 wherein the diamine is selected from the group consisting of ethylene diamine, hexamethylene diamine, a 4-aminobenzylamine, 4,4'-diaminodicyclohexyl methane, a phenylene diamine, a toluene diamine, 4,4'-methylene bis(2-chloroaniline), 4,4'-diaminodiphenyl sulfone, 4,4'-diaminodiphenyl ether and mixtures thereof.

* * * * *

UNITED STATES PATENT AND TRADEMARK OFFICE
CERTIFICATE OF CORRECTION

PATENT NO. : 5,221,724
DATED : June 22, 1993
INVENTOR(S) : Chi Li and Stuart L. Cooper It is certified that error appears in the above-indentified patent and that said Letters Patent is hereby corrected as shown below:

Column 7, line 44, change "LSL-11" to --LSI-11--.

Column 7, line 64, change "0.35 1/ÅA" to --0.35 1/Å--.

Column 7, line 64, change "where 0" to --where θ--.

Signed and Sealed this

Twenty-sixth Day of July, 1994

Attest:

BRUCE LEHMAN

*Attesting Officer*     *Commissioner of Patents and Trademarks*